(12) United States Patent
Hoctor et al.

(10) Patent No.: US 9,366,753 B2
(45) Date of Patent: Jun. 14, 2016

(54) SYSTEMS AND METHODS FOR ULTRASOUND RETROSPECTIVE TRANSMIT FOCUS BEAMFORMING

(71) Applicant: General Electric Company, Schenectady, NY (US)

(72) Inventors: Ralph Thomas Hoctor, Saratoga Springs, NY (US); Daniel John Buckton, Zipf (AT); Srinivasan Jagannathan, Niskayuna, NY (US); Martin Paul Mienkina, Neumarkt am Wallersee (AT); Jing Jin, Schenectady, NY (US)

(73) Assignee: General Electric Company, Niskayuna, NY (US)

( * ) Notice: Subject to any disclaimer, the term of this patent is extended or adjusted under 35 U.S.C. 154(b) by 262 days.

(21) Appl. No.: 13/970,358

(22) Filed: Aug. 19, 2013

(65) Prior Publication Data

US 2015/0049578 A1 Feb. 19, 2015

(51) Int. Cl.
*G01S 7/52* (2006.01)
*A61B 8/00* (2006.01)

(52) U.S. Cl.
CPC ......... *G01S 7/52085* (2013.01); *G01S 7/52046* (2013.01); *A61B 8/4444* (2013.01); *G01S 7/52095* (2013.01)

(58) Field of Classification Search
CPC ............ G01S 7/52046; G01S 7/52085; G01S 7/52095; A61B 8/52; A61B 8/5215
See application file for complete search history.

(56) References Cited

U.S. PATENT DOCUMENTS

| 5,897,501 A | 4/1999 | Wildes et al. |
| 7,297,118 B2 | 11/2007 | Kristoffersen |
| 8,241,216 B2 | 8/2012 | Loftman et al. |
| 8,317,712 B2 | 11/2012 | Burcher et al. |
| 2010/0217124 A1 | 8/2010 | Cooley |
| 2011/0270086 A1 | 11/2011 | Hoctor et al. |
| 2012/0004545 A1 | 1/2012 | Ziv-Ari et al. |

OTHER PUBLICATIONS

Vasudevan, "Ultrasonic Digial Beamformation : A Comparative Study", A thesis submitted to the Faculty of Graduate Studies and Research in partial fulfilment of the requirements of the degree of Masters of Engineering, McGill University, Sep. 14, 1998.

Jeong et al., "Beamforming using the Synthetic Sine Wave for Ultrasonic Imaging System", 2001 IEEE Conference—Ultrasonics Symposium, vol. 2, pp. 1539-1542, 2001.

Hergum et al., "Parallel Beamforming using Synthetic Transmit Beams", IEEE Transactions on Ultrasonics, Ferroelectrics and Frequency Control, vol. 54, issue 2, pp. 271-290, Feb. 2007.

*Primary Examiner* — Michael Rozanski
(74) *Attorney, Agent, or Firm* — Seema S. Katragadda

(57) ABSTRACT

Systems and methods for ultrasound beamforming are provided. One method includes obtaining ultrasound data using receive line spacing that changes as a function of depth, determining a number of transmit events to combine at each of a plurality of points for use in combining the obtained ultrasound data, and aligning the ultrasound data with time delays computed from a probe geometry used to obtain the ultrasound data. The method also includes combining the aligned ultrasound data to generate an ultrasound image.

30 Claims, 5 Drawing Sheets

SYSTEMS AND METHODS FOR ULTRASOUND RETROSPECTIVE TRANSMIT FOCUS BEAMFORMING

BACKGROUND

Diagnostic medical imaging systems typically include a scan portion and a control portion having a display. For example, ultrasound imaging systems usually include ultrasound scanning devices, such as ultrasound probes having transducers that are connected to an ultrasound system to control the acquisition of ultrasound data by performing various ultrasound scans (e.g., imaging a volume or body). The ultrasound probes typically include an array or matrix of transmit/receive elements, which transmit ultrasound waves and receive back-scattered echo signals. The ultrasound systems are controllable to operate in different modes of operation and to perform different scans. The received signals are then processed to generate images for display to a user.

Different beamforming techniques may be used to synthetically modify the effective transmit beam used by ultrasound systems to acquire ultrasound data that is used to generate the images. For example, Retrospective Transmit Beamforming (RTB) is used to form a synthetically focused ultrasound image using standard, scanned, and focused ultrasound transmissions. More particularly, RTB is a synthetic focus technique that uses standard, scanned-beam transmit data, dynamic receive focusing, and combination of time-aligned data from multiple transmits to form images.

One variation of the standard architecture of an ultrasound system employs a dynamically focused, multi-line acquisition (MLA) beamformer, which produces multiple receive beamformed output signals for each transmit. Such a system allows a broad transmit beam to be used to illuminate the reflectivity distribution, while more than one narrow receive beam is used to produce data for image generation. Two-stage RTB is an implementation of the RTB technique wherein the first stage implements high-MLA receive beamforming and the second stage implements a combination of receive data from different transmits. In known systems, the receive data is recorded in straight lines, with successive samples representing increasing depths at the same beam steering angle. Also in known systems, the data is aligned using some form of model of the high-power portion of the physical transmit beam, which limits the application of RTB at the transmit focal depth.

Moreover, in these known systems, the number of transmit events (or transmits) to combine at every image location is dictated by the applicability of the data alignment scheme. In general, RTB solves the problem of de-focusing of an ultrasound image at depths different from the transmit focal depth. In some other known systems, this issue is addressed by performing multiple transmits in each look direction, each focused at a different depth, and using each to form a separate depth zone of the image. However, this slows the frame rate, and, thus, negatively affects the overall performance of the system.

BRIEF DESCRIPTION

In one embodiment, a method is provided that includes obtaining ultrasound data using receive line spacing that changes as a function of depth, determining a number of transmit events to combine at each of a plurality of points for use in combining the obtained ultrasound data, and aligning the ultrasound data with time delays computed from a probe geometry used to obtain the ultrasound data. The method also includes combining the aligned ultrasound data to generate an ultrasound image.

In another embodiment, an ultrasound system is provided that includes a probe configured to acquire ultrasound data and a controller configured to control acquisition of the ultrasound data by the probe and process the acquired ultrasound data. The controller includes a retrospective transmit beamforming (RTB) module configured to perform the method described above.

DETAILED DESCRIPTION

Figure 1:
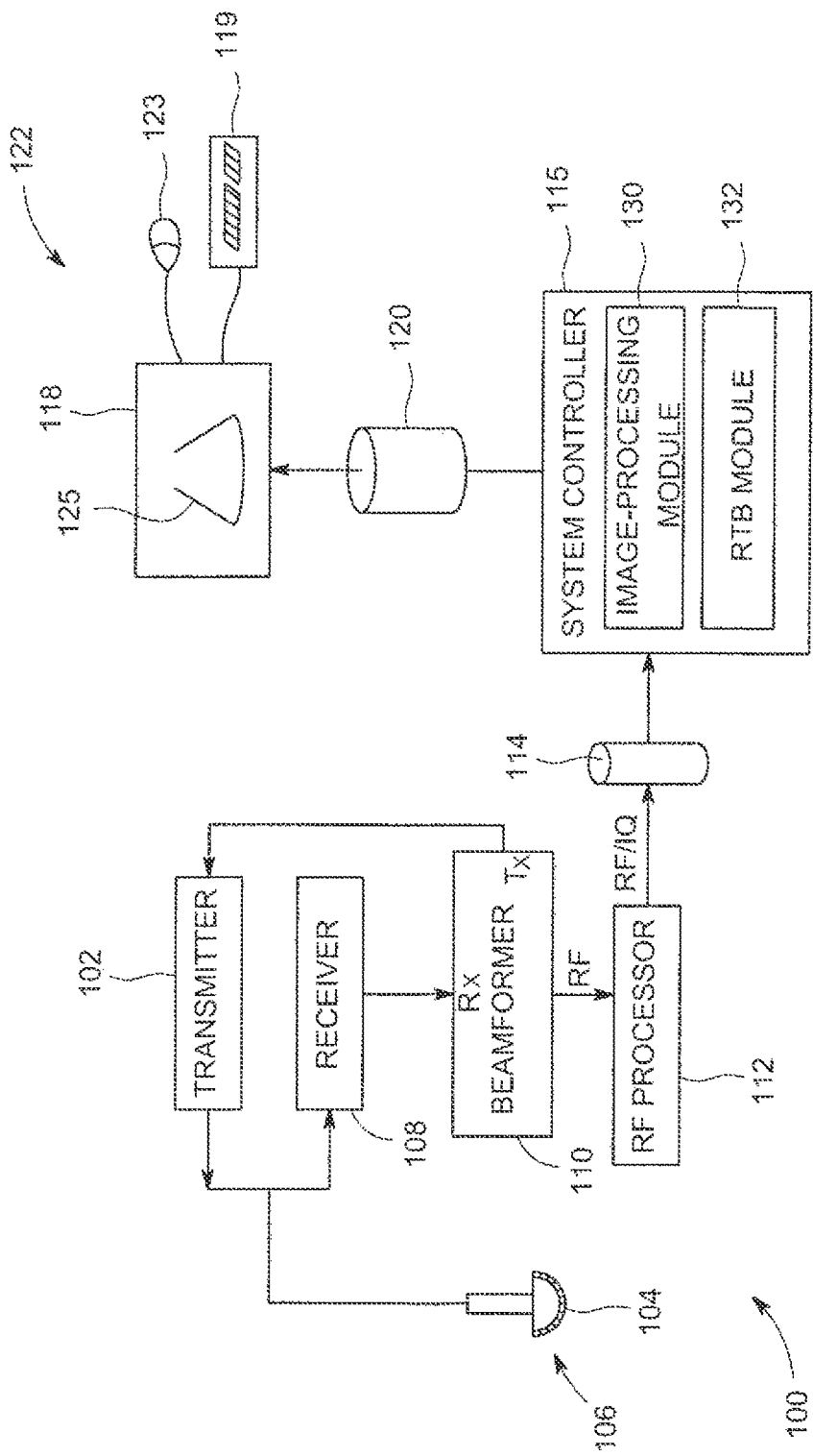
FIG. 1 is a block diagram of an ultrasound system in accordance with an embodiment.

Various embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors, controllers, or memories) may be implemented in a single piece of hardware (e.g., a general purpose signal processor or random access memory, hard disk, or the like) or multiple pieces of hardware. Similarly, any programs may be stand-alone programs, may be incorporated as subroutines in an operating system, may be functions in an installed software package, and the like. It should be understood that the various embodiments are not limited to the arrangements and instrumentality shown in the drawings.

As used herein, the terms "system," "unit," or "module" may include a hardware and/or software system that operates to perform one or more functions. For example, a module, unit, or system may include a computer processor, controller, or other logic-based device that performs operations based on instructions stored on a tangible and non-transitory computer readable storage medium, such as a computer memory. Alternatively, a module, unit, or system may include a hard-wired device that performs operations based on hard-wired logic of the device. The modules or units shown in the attached figures may represent the hardware that operates based on software or hardwired instructions, the software that directs hardware to perform the operations, or a combination thereof.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Generally, various embodiments provide Retrospective Transmit Beamforming (RTB) that performs data alignment and produces sharper focus in the near zone as a result of decreased phase noise in the data summation. Various embodiments also avoid far-zone sampling problems of some conventional schemes. In operation, the number of transmit events (also referred to as transmits) to combine at any point is determined by the peak power of the incident waveform at that point of each the transmits, which results in the ability to combine more transmits throughout the image, compared to known schemes. Additionally, receive data is not constrained to be measured on a common sampling grid for each transmit, wherein coherent interpolation of the complex baseband representation of the measured signal is used to transfer each set of received data onto a common sampling grid for addition, allowing the use of dynamic beam steering as part of the receive data beam formation in a first stage of a two-stage process. As a result, various embodiments can continuously increase the lateral (angular) density of sampled points with greater depth, as the number of transmits suitable for RTB combination decreases.

At least one technical effect of various embodiments is performing RTB at a higher frame rate than existing system. At least one other technical effect of various embodiments is a simpler implementation than other synthetic focus schemes using a standard transmission scheme for RTB. At least one additional technical effect of various embodiments is a more highly focused image with no decrease in frame rate. At least one additional technical effect of various embodiments is an increase in the depth to which a sector scan image can extend without lateral under-sampling artifacts.

Embodiments described herein include systems, methods, and computer readable media that may be used to perform RTB. The image data is obtained in various embodiments using an ultrasound imaging system.

FIG. 1 illustrates a block diagram of a system 100 according to one embodiment. In the illustrated embodiment, the system 100 is an imaging system and, more specifically, an ultrasound imaging system. However, it is understood that embodiments set forth herein may be implemented in combination with other types of medical imaging modalities (e.g., MR. CT, PET/CT, etc.). Furthermore, it is understood that other embodiments do not actively acquire medical images. Instead, embodiments may retrieve image data that was previously acquired by an imaging system and analyze the image data as set forth herein. As shown, the system 100 includes multiple components. The components may be coupled to one another to form a single structure, may be separate but located within a common room, or may be remotely located with respect to one another. For example, one or more of the modules described herein may operate in a data server that has a distinct and remote location with respect to other components of the system 100, such as a probe and user interface. Optionally, in the case of ultrasound systems, the system 100 may be a unitary system that is capable of being moved (e.g., portably) from room to room. For example, the system 100 may include wheels, be transported on a cart or may be a handheld or hand-carried device.

In the illustrated embodiment, the system 100 includes a transmitter 102 that drives an array of elements 104, for example, piezoelectric crystals, within a diagnostic ultrasound probe 106 (or transducer) to emit pulsed ultrasonic signals into a body or volume (not shown) of a subject. The elements 104 and the probe 106 may have a variety of geometries. The ultrasonic signals are back-scattered from structures in the body, for example, blood vessels and surrounding tissue, to produce echoes that return to the elements 104. The echoes are received by a receiver 108. The received echoes are provided to a beamformer 110 that performs beamforming and outputs an RF signal. The RF signal is then provided to an RF processor 112 that processes the RF signal. Alternatively, the RF processor 112 may include a complex demodulator (not shown) that demodulates the RF signal to form IQ data pairs representative of the echo signals. The RF or IQ signal data may then be provided directly to a memory 114 for storage (for example, temporary storage).

The system 100 also includes a system controller 115 that includes a plurality of modules, which may be part of a single processing unit (e.g., processor) or distributed across multiple processing units. The system controller 115 is configured to control operation of the system 100. For example, the system controller 115 may include an image-processing module 130 that receives image data (e.g., ultrasound signals in the form of RF signal data or IQ data pairs) and processes image data. For example, the image-processing module 130 may process the ultrasound signals to generate slices or frames of ultrasound information (e.g., ultrasound images) for displaying to the operator. The image-processing module 130 may be configured to perform one or more processing operations according to a plurality of selectable ultrasound modalities on the acquired ultrasound information. By way of example only, the ultrasound modalities may include color-flow, acoustic radiation force imaging (ARFI), B-mode, A-mode, M-mode, spectral Doppler, acoustic streaming, tissue Doppler module, C-scan, and elastography. The generated ultrasound images may be two-dimensional (2D) or three-dimensional (3D).

Acquired ultrasound information may be processed in real-time during an imaging session (or scanning session) as the echo signals are received. Additionally or alternatively, the ultrasound information may be stored temporarily in the memory 114 during an imaging session and processed in less than real-time in a live or off-line operation. An image memory 120 is included for storing processed slices of acquired ultrasound information that are not scheduled to be displayed immediately. The image memory 120 may comprise any known data storage medium, for example, a permanent storage medium, removable storage medium, and the like.

In operation, an ultrasound system may acquire data, for example, volumetric data sets by various techniques (for example, 3D scanning, real-time 3D imaging, volume scanning, 2D scanning with transducers having positioning sensors, freehand scanning using a voxel correlation technique, scanning using 2D or matrix array transducers, and the like). Ultrasound images 125 may be displayed to the operator or user on a display device 118.

The system controller 115 is operably connected to a user interface 122 that enables an operator to control at least some of the operations of the system 100. The user interface 122 may include hardware, firmware, software, or a combination thereof that enables an individual (e.g., an operator) to directly or indirectly control operation of the system 100 and the various components thereof. As shown, the user interface 122 includes the display device 118. In some embodiments, the user interface 122 may also include one or more input devices, such as a physical keyboard 119, mouse 123, and/or touchpad. In one embodiment, the display device 118 is a touch-sensitive display (e.g., touchscreen) that can detect a presence of a touch from the operator and can also identify a location of the touch. The touch may be applied by, for example, at least one of an individual's hand, glove, stylus, or the like. As such, the touch-sensitive display may also be characterized as an input device that is configured to receive inputs from the operator. The display device 118 also communicates information to the operator by displaying the information to the operator. The display device 118 and/or the user interface 122 may also communicative audibly. The display device 118 is configured to present information to the operator during the imaging session. The information presented may include ultrasound images, graphical elements, user-selectable elements, and other information (e.g., administrative information, personal information of the patient, and the like).

In addition to the image-processing module 130, the system controller 115 may also include an RTB module 132, which in various embodiments is configured to control a two-stage RTB as described in more detail herein. The basic approach to RTB is to form an image directly from element-domain received data measured for each transmit, which is referred to as single-stage beamforming. Two-stage beamforming is an approximation to single-stage beamforming that reduces the number of data vectors to be transferred from the front-end to the receive beamformer (such as the beamformer 110, which may be a receive and transmit beamformer), which is accomplished by performing receive beamforming with multi-line acquisition (MLA) on the element data as a pre-processing step. It should be noted that as long as the number of receive lines produced per transmit is smaller than the number of array elements, the amount of data is reduced (beamformed data can also be sampled at a lower rate than element data.)

Various embodiments may be used with a probe 106 having a curved, translated-aperture array 104, such as used for women's health applications. However, other configurations are contemplated. This array has relatively widely spaced transmits for a sector scanning device that has such a large maximal imaging depth. The device uses MLA to ensure adequate angular sampling at larger depths.

Figure 2:
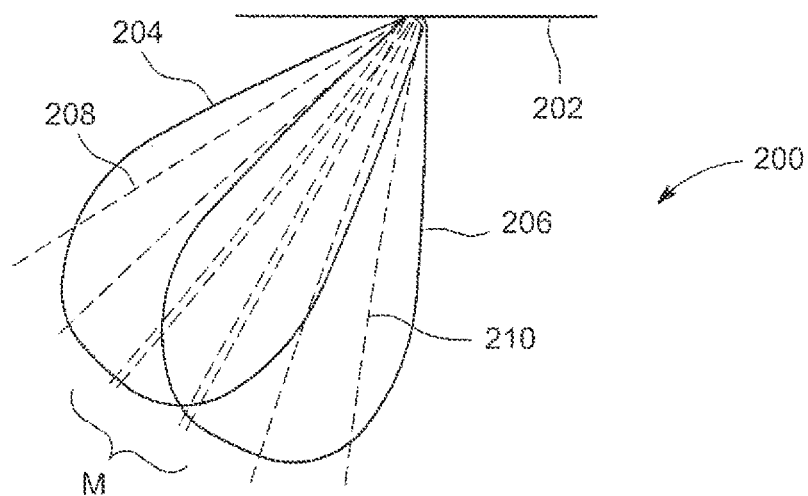
FIG. 2 is a diagram illustrating transmit beams and associated receive lines in a two stage Retrospective Transmit Beamforming (RTB) scheme in accordance with various embodiments.

The two-stage RTB beam spacing is illustrated in the image 200 of FIG. 2. The line 202 represents the array, and the solid closed curves 204 and 206 represent broad, adjacent, transmit beams. For example, the area enclosed by each curve 204 or 206 may be the region over which the echo from a point reflector can be expected to exceed a certain pre-determined signal-to-noise ratio. The dashed lines 208 and 210 represent receive lines, that is, represent a sequence of receive samples at every focal point of the dynamically focused receive beamformer. The middle two receive lines overlay each other and can be added on a sample-by-sample basis.

In general, a two-stage RTB system spaces the receive-beamformed lines widely enough to facilitate combination thereof, namely receive lines from different transmits must overlap if the receive lines are to be combined. This means that each sample from each of the receive lines is computed by a receive beamformer focused on the spatial location of the sample, which is the same spatial location for each transmit. As an example of the receive line spacing, consider the following: if data from eight adjacent transmits is to be combined, receive lines from transmit number one is spaced so that one or more of the lines overlap with receive lines of transmit number eight. In a 16-MLA system, this means that the receive line spacing is only half the transmit line spacing, and that the final MLA factor of the synthetically focused beams is 2-MLA. This is lower than obtained from the first stage in a standard MLA set-up by a factor equal to the maximum number of beams to be combined for RTB. The MLA factor of the synthesized RTB lines is referred to as the "output MLA", and distinct from the MLA factor supported by the first stage hardware, which is referred to as the "hardware MLA".

In RTB image formation, it is desirable to combine data from a larger number of transmits than performed with standard MLA beam formation. In the near zone, the combination of eight transmits produces a good RTB result, but in light of the above-described 16-to-1 first-stage hardware MLA limit, this limits the output MLA to 2-to-1, which is not good enough at the focal depth and beyond (although it can be adequate at shallow depths). On the other hand, the number of transmits that may be combined for improved focus and SNR decreases with depth, such that a trade-off may be made: the reduction in RTB combination requirement for higher output MLA at greater depths.

In particular, with respect to a single-stage RTB implementation, the input is time series data for each receive element. This data can be receive beamformed in any manner required by the RTB algorithm, for example by focusing on every sample location in the image to be reconstructed, which is sometimes called pixel processing because any pixel in any output image can be reconstructed directly from the input data, with receive focus exactly at the pixel location and without such intermediate operations as scan conversion. A single-stage implementation forms a receive-focused sample for each transmit to be used at the location to be reconstructed. The RTB algorithm applies an additional alignment delay and then the samples are added. Using the correct alignment delay can perceptibly improve the image focus, as described in more detail herein.

For typical two-stage implementations, receive beamformer samples must line up in space, so that at each sample location, the result is exactly like the one-stage result, in that the receive beamformer is focused at the same location for all samples that are added. The difference is that in the two-stage approach, the angular density of samples remains constant with depth (there are the same number of samples at every depth), while in a single-stage implementation, the angular density of samples can be varied with depth as needed. This is because, in the two-stage approach, samples are generated along "beam lines", which are straight lines radiating out from the phase center. Thus, if straight, equally spaced receive beams are used, some of the beams are not being used in deeper regions. This represents MLA beamformer computational power that may be applied to the spatial sampling problem.

Thus, standard receive beamformer spatial sampling schemes result in a marked reduction of output MLA in the two-stage RTB scheme. This becomes a noticeable image problem at deeper imaging depths, and constitutes a spatial sampling problem that can cause a scintillation artifact with probe motion. In various embodiments, sampling control is provided by dynamic beam steering in the first stage. In particular, because the number of transmits to combine for RTB decreases with depth, some output lines are not used at larger depths. These output lines are the receive lines that are the most widely separated from the transmit line in beam steering angle. So, in order to use more of the receive beamforming capacity at all depths and to provide a higher output MLA at larger depths, various embodiments change the angular sampling scheme to produce different line spacings at different depths. In this way, the output MLA is increased at depths where the RTB combination numbers are small enough to allow such a process.

Figure 3:
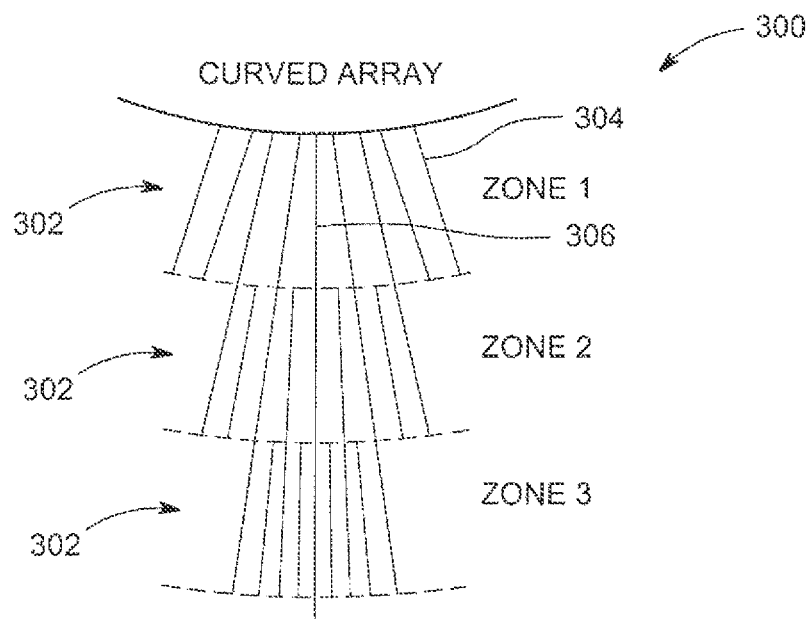
FIG. 3 is a diagram illustrating changes in receive line spacing in accordance with an embodiment.

Thus, in various embodiments, such a scheme is implemented with a receive beamformer (such as the beamformer 110), and uses dynamic beam steering in addition to dynamic focusing. FIG. 3 illustrates such a sampling scheme 300. In particular, the data set is divided into multiple zones 302 (illustrated as zones 1, 2, 3), each with a corresponding range of imaging depths, and each with a respective receive line angular spacing. For example, in zone 1, 8-RTB is provided, which means that data from eight separate transmits (illustrated by the MLA lines 304) is combined to form every RTB output line. The receive lines are spaced by the same angular separation as the transmit lines, so seven of the eight receive lines line up with the receive lines from the two adjacent transmits, six out of eight for the transmits two over, and so on. Each receive line is replicated for each of eight transmits, and the eight lines are added after imposition of the alignment delays as is known. In zone 2, the outer four receive lines are too far from the transmit to be used in the reconstruction, such that zone 2 is limited to 4-RTB. In this zone, receive lines in the region around the transmit are generated to give a higher angular density of receive lines. For example, in the illustrated embodiment, these lines are spaced at half the angular spacing of the transmit line and line up with only the receive lines from the adjacent three transmits, whereas the receive lines in zone 1 line up with the adjacent seven. Thus, four lines are added together to form each output line, and the output lines are spaced at half the angular spacing of those in zone 1. In zone 3, another factor of two reduction in spacing is provided, and lines are co-linear with the line of only one other transmit, such that 2-RTB is implemented. It should be noted that there is no receive line directly in the transmit beam steering direction. It also should be noted that the line 306 represents the transmit beam direction or position. Thus, the beamformer 110 in various embodiments is configured to receive data along the lines 304 as the line 306 is moved or steered.

Figure 4:
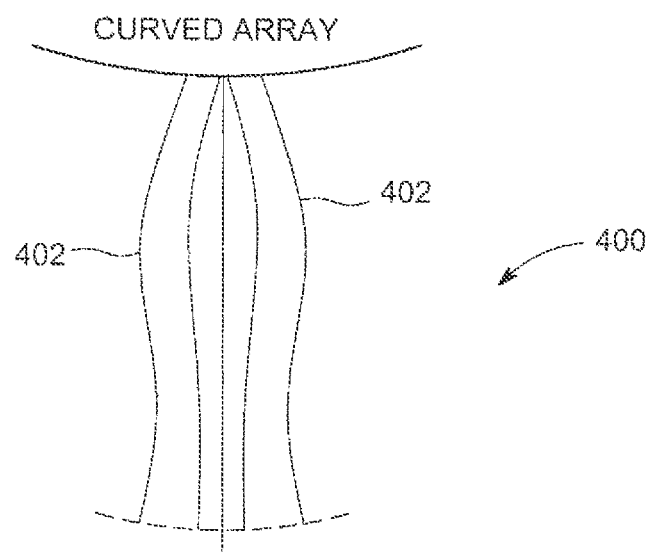
FIG. 4 is a diagram illustrating changes in receive line spacing in accordance with another embodiment.

Thus, by steering the receive lines during the time of flight of the transmitted pulses, the lateral spacing of the receive lines is changed. Accordingly, number and density of samples contained in the overlap with the next transmit is increased. It should be noted that although FIG. 3 illustrates discontinuous changes in receive line spacing on the three range zones, a continuous dynamic beam steering scheme 400 may be implemented as illustrated in FIG. 4, combined with complex interpolation. For example, as can be seen in FIG. 3, there are several lines 304 that start in the middle of the image, and only two lines that are continuous through all three zones 304. Such discontinuities can cause ringing with any filters that try to filter an entire line. The result of this may be bands in the image at the zone boundaries. While this effect may be reduced or minimized using signal processing techniques in the art, such as with a spatially-varying filter, various embodiments provide sampling control by continuous dynamic beam steering with complex interpolation.

In particular, various embodiments address the problem of discontinuities using continuously varying dynamic beam steering in addition to dynamic focusing. In the illustrated embodiment of FIG. 4, the receive lines 402 are curved in space, and are closer to one another in the same general way as the discontinuous spacing changes as illustrated in FIG. 3, but with limited sample-to-sample spatial location change to provide a continuous output signal (resulting from correlated samples of the reflectivity distribution). It should be noted that the limitation of the sample-to-sample location change is equivalent to a limitation on the rate of change of the beam steering angle. Although this provides a continuous output, the samples for one transmit do not line up with the samples of any other transmit under this scheme, unlike the previous scheme in FIG. 3. Thus, in the scheme 400, the RTB vector addition can no longer be performed in a one-dimensional buffer. Accordingly, in this embodiment, the recorded lines are interpolated to a two-dimensional region and a complex image addition of images formed from the complex baseband signal of the recorded data is performed. Thus, in this embodiment, complex images are added together.

Accordingly, FIG. 4 illustrates a set of curved, continuous, receive lines 402 associated with a single transmit. (The measured signal is discrete; these continuous lines map out the location of a sequence of discrete samples that lie along the line). FIG. 4 illustrates four lines, but the number used is determined by the capability of the MLA receive hardware, and in various embodiments the largest number of such lines is used. As described herein, the measured samples on these lines 402 do not line up with the samples of other transmits, such that the received data is interpolated to a common set of image sample points prior to RTB combination. In one embodiment, a rectilinear, whole-image sampling grid is defined, with the locations of every sample on the curved receive lines 402 of FIG. 4 known relative to the sample grid. The portion of the whole-image sample grid that lies between the two outside receive lines for each transmit is filled in with data interpolated from the receive lines. The resulting partial image is then be added to a buffer containing the (incomplete) reconstructed image. Because this addition is coherent in order to obtain the benefits of synthetic focus, conversion to complex I/Q signal representation is used to capture the phase and envelope at each sample. Alignment delays are again used on the measured samples before two-dimensional interpolation. The alignment delays can either be provided by modifying the phase of the I/Q samples (narrowband approximation) or by a point-wise-sampling of the whole RF signal prior to Ii/Q conversion. This complex 2D interpolation is an extension of the interpolation that can be performed on linear A-lines in the second stage of a two-stage RTB scheme to implement alignment delays. (This applies to a system in which the alignment delays are not applied in the first-stage MLA receive beamformer).

It should be noted that in various embodiments, combination in 2D or 3D may be provided. Additionally, in some embodiments, partial images are not formed and combined, but instead, for example, the buffering step (generating partial images) is omitted and the ultrasound image is formed by sequentially reconstructing the output point by point. For example, some embodiments may determine for each of a plurality of points (e.g., data points) a position in space, determine output pixels for the ultrasound image by selecting a plurality of nearest points (e.g., neighbor points within a defined pixel range) from each of a plurality of receive lines, and summing the plurality of nearest points.

It should be noted that while the schemes described herein are discussed in the context of a curved array, the schemes may be implemented with other types of arrays, such as phased arrays or to any sector-scan probe, among others. Thus, various embodiments may be implemented with any sector-scan system in which dynamically focused MLA beamforming is performed in a first stage, and a combination of the received lines into synthetically focused data occurs at a second stage, with the second stage operating on the receive beamformed data generated by the first stage. In such a two-stage RTB system, the output receive lines are synthesized by the addition of data from multiple MLA lines produced by the first stage. Such data can be RF or I/Q, but after addition, the data is converted into intensity data. Regardless of the signal representation selected for the data, the data in various embodiments retains phase information. It should be noted that two samples of I/Q data can be added directly if the carrier phase used to convert the I/Q to RF is the same for both samples. If this is not the case, the carrier phase is computed for each and the I/Q sample converted to an analytic signal sample prior to addition. After generation of the synthetically focused receive lines, the signal envelope is extracted and the image is generated by scan conversion from the resulting real-valued data using methods in the art.

In various embodiments, to perform a complex image addition scheme, a set of curved MLA receive lines that cover the higher-SNR region defined by each transmit are used. Referring back to FIG. 2, this higher SNR region may be described by one of the closed curves 204 or 206. Since the curved receive lines from separate transmits may not align with each other, the data from each set is coherently interpolated onto a uniform sample grid, so that data from separate transmits can be added. Each interpolated data set forms a complex image in which only the pixels associated with a single transmit are non-zero. The set of MLA lines cover the region uniformly, at a sample density that allows the set of MLA lines to be interpolated. The location of the non-zero portion of each image is determined by the width and steering angle of the transmit beam, and beams that are widely separated in angle will have no common pixels. If the transmits are performed sequentially in beam steering angle, then the images having common non-zero pixels are maximally correlated with respect to the state of the reflectivity distribution.

Different means for specifying the spatial trajectories of the receive beams to cover the transmit beam for use in RTB combination will now be described. In particular, for any sector scan, including that produced by a probe with a curved surface geometry, the line spacing increases as the depth increases. The difference between a phased array sector scan and a curved array sector scan is that the curved array produces a uniform beam width with sector scan angle. To provide receive line spacing that is not larger than the receive beam width, a different MLA line density may be used at different image depths. The effective MLA number per transmit (output line density) is determined by both transmit and receive beam patterns. If it is assumed, for example, that the maximum MLA number per transmit is 16, and if the number of beams to be combined is N, which is a function of transmit beam spacing and depth, then the effective MLA per transmit is $$eMLA = \frac{16}{N(\theta_{TX}, r)},$$

where $\theta_{TX}$ is the transmit beam angular spacing, and r is range. The angular spacing of the effective MLA is defined as:

$$\theta = \theta_{TX} * N(\theta_{TX}, r)/16 \quad (1)$$

To avoid spatial aliasing, $\theta$ should also satisfy:

$$2r\tan(\theta/2) \approx r*\theta \le \lambda * F(r) \quad (2)$$

where F denotes the depth dependent receive f-number (note that the receive beam is dynamically focused), and $\lambda * F(r)$ is the approximate receive beamwidth. Combining Equations (1) and (2), the largest allowable receive line spacing can be calculated, and then the maximum transmit spacing $\theta_{TX}$ can be determined under a given receive aperture apodization (f-number). To provide that the receive line spacing is smaller than the receive beam width at every depth in one embodiment, the maximum transmit spacing $\theta_{TX}$ is, for example, 0.5 degrees for straight MLA lines case, and 1.2 degrees for dynamic steering MLA lines, which means the frame rate can be doubled through the use of dynamic beam steering. However, other angles may be used for one or both.

Figure 5:
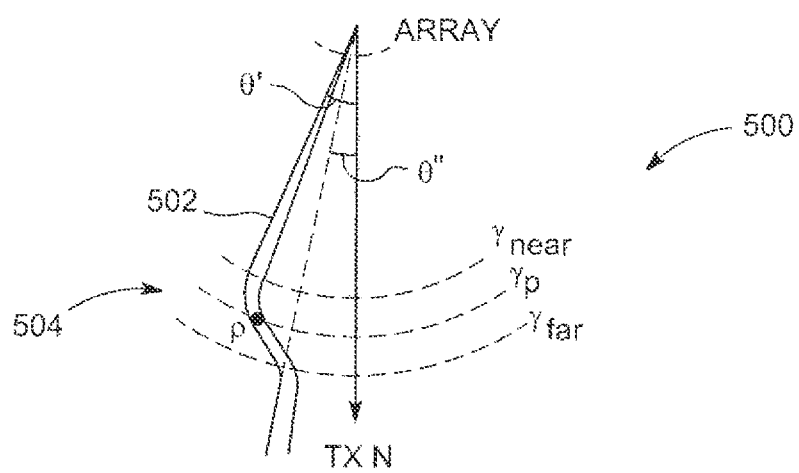
FIG. 5 is a diagram illustrating the geometry of dynamically beam steered receive lines in accordance with various embodiments.

One way to implement this MLA density change is using dynamic beam steering in addition to dynamic focus to make a gradual transition from a lower MLA line density zone to a higher density zone to avoid abruptly changing of steering direction. The transition curve can be defined as shown in FIG. 5 illustrating the geometry 500 of dynamically beam steered receive lines 502. For example, the MLA angular spacing is $\theta$ before range $r_{near}$, and decreases to $\theta'$ after range $r_{far}$. The curve 502 that connects $r_{near}$ and $r_{far}$ can be defined as:

$$r_n = r_{near} + n\Delta \quad (3)$$

$$\theta_n = \theta - n * \frac{\theta - \theta_r}{(r_{far} - r_{near})/\Delta} \quad (4)$$

$$\text{where } \Delta = \frac{c}{f_s}/2,$$

is the range sampling spacing.

To reconstruct an image point p in the curved zone 504, two points which are on the neighboring curve lines with the same range $r_n = r_p$, and the smallest $|\theta_n - \theta_p|$ are linearly interpolated.

The computation of alignment delays will now be described. It should be noted that any number of beams can be combined at any depth using the various embodiments, but in regions where the transmit beam is very defocused, this only adds noise to the image. Thus, described below are methods selecting the number of beams to combine as a function of depth.

Figure 6:
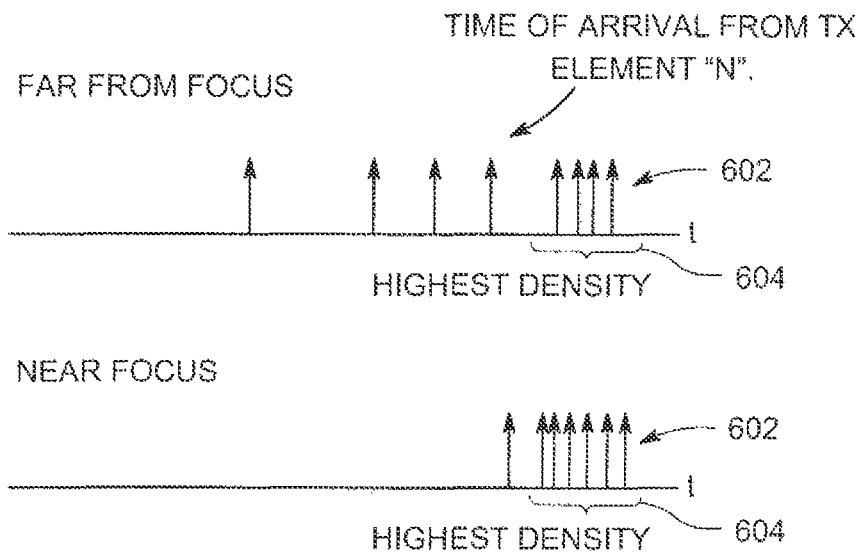
FIG. 6 is a diagram illustrating data alignment delay computation in accordance with various embodiments.

In regions away from the transmit focus of a focused ultrasound beam, the incident waveform is stretched out in time, and the peak power delivered to the point is low, compared with that delivered at the transmit focus. The incident waveform is the superposition of wavelets, one from each transmit element, and so the set of propagation times from the transmit elements to the point to be reconstructed determines the shape of the incident waveform. The reflection from the point of interest has the form of the incident waveform. The delays are computed for a specific point of interest at which the reflectivity is estimated and for each of a set of focused transmits from which data is to be combined. FIG. 6 illustrates a process or algorithm for computing data alignment delays.

In particular, FIG. 6 is a schematic depiction of one step of the algorithm for two points in the image, one near the transmit focus, where most of the wavelets combine constructively, and another farther from the focus, where the wavelets are more spread out in time resulting in less constructive (in-phase) combination. First, the delays from the point of interest to each of N transmit elements are computed using the nominal speed of sound of the system or some predetermined estimate of the sound speed, and the transmit beam steering and focusing delays applied to each element are then added. This gives a set of delays $\{d_1, \ldots, d_N\}$ with one delay for each transmit element.

Next, the delays are sorted, which are illustrated as upward pointing arrows 602 in FIG. 6. Thereafter, a search is performed for the largest subset of the delays that are contained within a time window 604 of a given size, for example, 100 nanoseconds, which is approximately a quarter period (at center frequency) for some exemplary systems (4 MHz and 4.34 MHz system), such that arrivals that occur within such an interval are highly coherent. The final value produced by the algorithm is the mean of the delays in the window 604 at the time location encompassing the largest number of delays. This represents an estimate of the reflection time of the highest peak-power segment in the incident waveform, and may be referred to a Maximum Peak Power (MPP) approach.

Figure 7:
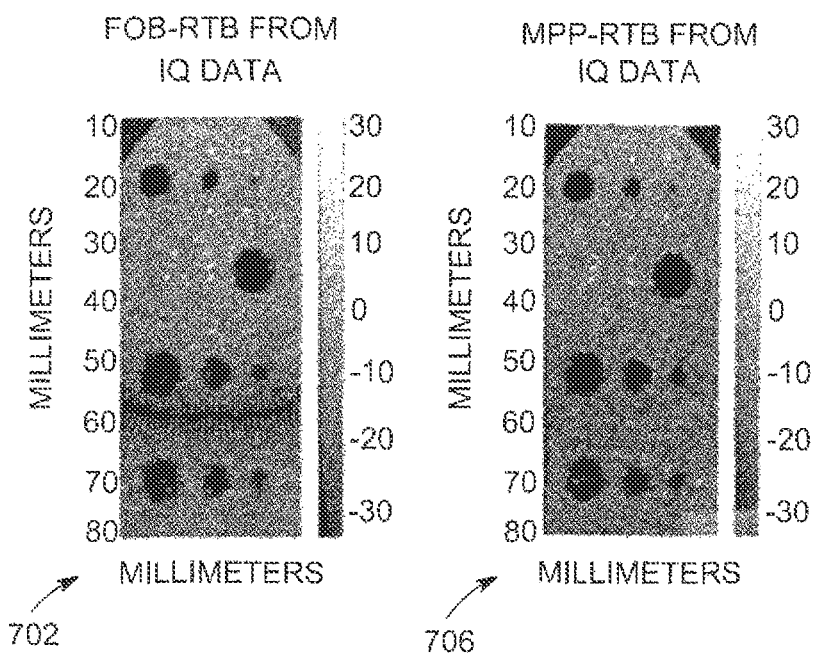
FIG. 7 illustrates images generated using different beamforming methods.

In operation, when selecting data to be combined for RTB, the MLA receive beamformer output data vector is indexed using the sum of a transmit and receive delay. The receive delay is the phase center delay of the sample, assuming a phase-center-referenced receive delay structure. The transmit delay is the delay computed as described above. This value corresponds to the time delay of largest number of coherently superposed wavelets, which is well-defined everywhere, not just in regions where a converging wavefront exists. In one embodiment, the data alignment delay scan be incorporated into field-programmable gate array (FPGA) receive beamforming delays. This is possible because each sample of each output line from the receive beamformer is used only once in an RTB combination. Alternatively, the receive lines can be sampled using a phase center reference and the result re-sampled to incorporate the difference between the alignment delays and the phase center referenced delays at every point, in the second stage, prior to addition. FIG. 7 illustrates an image 702 generated from simulations using one conventional approach, and an image 706 generated from simulations using various embodiments described herein. It should be noted that the images represent single stage results, namely using a single stage pixel processor that inputs element data from a number of transmits and outputs a set of RTB samples in a rectilinear grid. All three images were generated using the same simulated data. The simulated array is a generic, 4-MHz, 64-element phased array with approximately 0.6λ element spacing, rather than a simulation of an actual probe. Eighty-one transmit beams are spaced at one degree over a 80-degree sector, and the transmit focus is set to 6 cm. I/Q data was generated at a 10 MHz sample rate, and the receive beamformer uses a 4-point band-limited interpolation filter to up-sample to an effective analytic signal sampling rate of 400 MHz in the beam summation. The data alignment delay (transmit delay) was computed in one of two ways: the Frazier and O'Brien (FOB) approach (e.g., as described in C. H. Frazier and W. D. O'Brien, "Synthetic aperture techniques with a virtual source element", *IEEE Trans. On Ultrasonics, Ferroelectrics and Frequency Control*, vol. 45, pp. 196-207. January 1998) for image 702, and the MPP approach of various embodiment for image 706. The receive delay structure was dynamic receive focusing on the point of interest (pixel processing).

A maximum of fifteen transmits were combined, and the number of transmits combined varied with depth for all three methods. In the FOB approach this number is determined by the wavefront extent: only when a coherent wavefront from a given transmit passes over the location to be reconstructed can that transmit be used in the synthetic focus sum, and this qualification is computed by the algorithm. In the MPP approach, the number of transmits combined is determined by a minimum transmit peak power threshold, computed as part of the algorithm described in connection with FIG. 6, and as described in more detail herein.

Thus, the image 702 demonstrates the inability of the FOB approach to form an image near the receive focus, wherein the image was formed in a region of interest that excluded the transmit focus. In the near zone, up to about 4.5 cm, it is very difficult to tell the difference between the two images. The MPP approach, however, is not limited in how many transmits can be combined (at least not by the data alignment approach).

It should be noted that in any RTB scheme, motion of the reflectivity distribution limits the number of transmits that can be combined at any point. In various embodiments, a scheme is used that is based on the observation that the transmit beam width also limits the number of transmits that should be combined at any given depth. At any point to be reconstructed, the various transmit beams illuminate that point with more or less defocused incident waveforms. When the incident waveform is very elongated in time (defocused), the peak signal to noise ratio (SNR) of the reflection is low, no matter how the time alignment is computed. Data of lower SNR will add less to the reconstruction at a given point than data of higher SNR. The peak SNR at any given point can be estimated using the incident pulse rule: the peak power level from each beam is measured by the number of Tx path events occurring in a short window. The maximum such number, found by searching over start times of a window, can be used to estimate a maximum SNR, and a threshold can be defined, such that transmits with SNRs lower than the threshold do not contribute to the reconstruction.

With respect to computing the number of beams to combine with depth, in the MPP scheme, it is possible to combine any number of transmit beams at any point in the image. However, from a practical standpoint in a two-stage system, the number of output MLAs the system can produce for any transmit is the determining factor and, as a consequence, is the minimum spacing desired to be maintained between receive MLAs for avoiding any spatial aliasing artifacts. Depending on the application, the number of transmit beams to be combined with the depth in the image may be varied.

In simulations of a curvilinear probe, also referred to as a curve linear probe (e.g., a large curvilinear probe suitable for women's health applications), the following criterion was used for determining whether a certain transmit beam could be used for RTB: a transmit beam is "useful" for RTB reconstruction of a point if the number of arrivals within the 100-nanosecond time window used for computing the alignment delays for that point, exceeds 60% of the number of active transmit elements used in the transmit beam. The value "60%" was empirically chosen, based on the best performance of RTB in comparison to STB. (It should be noted that that the pixel processor simulations of FIG. 7 used 40% as the threshold). Because the time window is less than half of the period at the center frequency (230 ns), this corresponds to 60% of the transmit wavelets adding approximately constructively, and so constitutes a threshold applied to the peak power. The exception to this empirical criteria was in the first 3 cm where all maximum available transmits (8 in the illustrated case) were used for RTB. The minimum number of transmits to be combined in various embodiments is the two.

Figure 8:
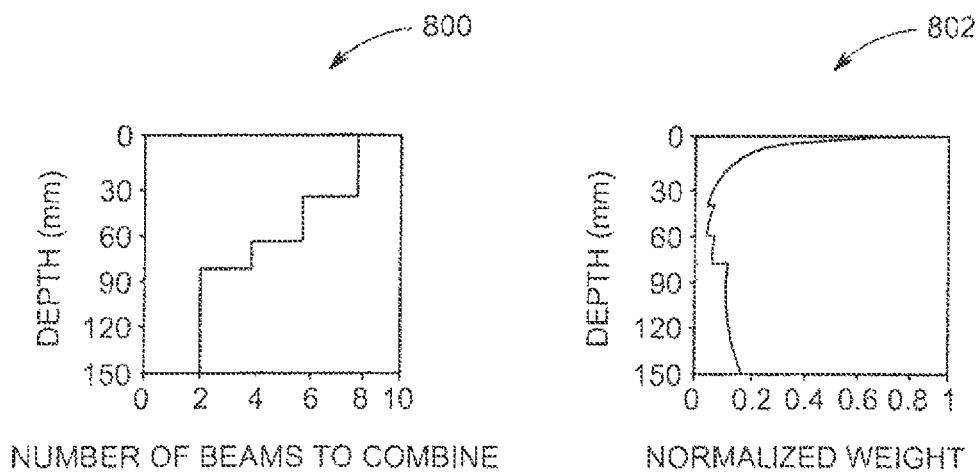
FIG. 8 illustrates graphs showing an exemplary number of transmit beams used and corresponding gain compensation in accordance with an embodiment.

The resulting image is then normalized by the total incident peak power (which changes with depth) in order to remove any artifacts due to discrete changes in the number of transmit lines combined with depth. FIG. 8 shows graphs 800 and 802 corresponding to the number of transmit beams combined with depth and the corresponding normalized incident power as a function of depth for the large curvilinear probe suitable for women's health applications, respectively. The focal depth for this simulation was at 12 cm and the number of transmit elements per transmit line was 72. (In the pixel processor implementation of FIG. 7, the number of transmit beams to combine is not limited to powers of two by the first stage beamformer. In the case of FIG. 7, a slight decrease of TGC was used to equalize the image intensities, without an explicit computation of total power).

Thus, a two-stage implementation for RTB may be provided that uses only geometrical factors to compute the alignment delays, and does not use any beamshape modeling. Accordingly, the alignment of data in various embodiments is performed using criteria that use knowledge of the probe geometry and assumption of a nominal speed of sound. Moreover, the number of transmits to combine at every point is determined by the SNR of the data to be combined, and not by the limitations of the alignment scheme.

Figure 9:
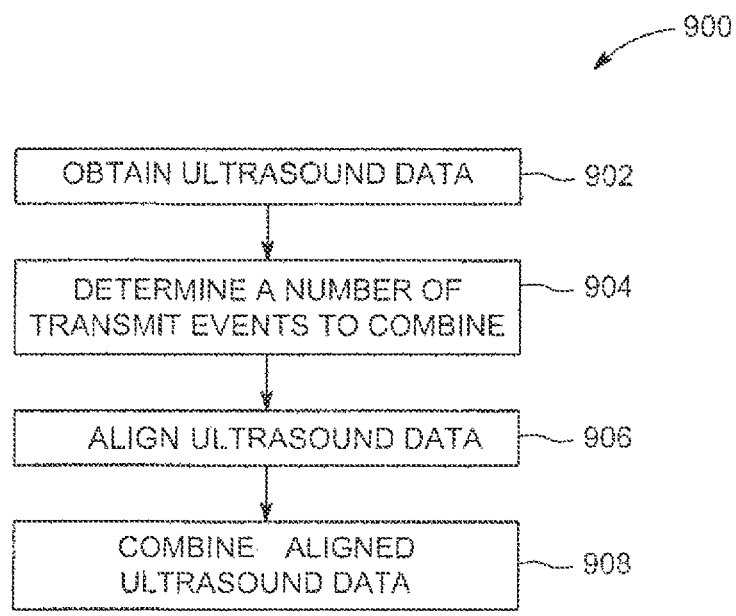
FIG. 9 is a flowchart of a method in accordance with an embodiment.

A method 900 for RTB in accordance with various embodiments is shown in FIG. 9. The method 900 includes obtaining ultrasound data at 902, which may be presently acquired data or stored data that was previously acquired. It should be noted that the received data from each transmit is formed into a number of A-lines (e.g., axial lines relative to the probe) in the first stage in accordance with various embodiments. The method 900 also includes determining a number of transmit events to combine at 904. For example, at each of a plurality of points a number of transmit events to combine are determined for use in combing the ultrasound data.

The method further includes at 906 aligning the ultrasound data. For example, the obtained ultrasound data may be aligned with time delays computed from the probe geometry used to obtain the ultrasound data. The aligned ultrasound data is then combined at 908 to generate an ultrasound image as described in more detail herein.

It should be noted that if the ultrasound data is complex beamformed data, then the data may be interpolated, which in various embodiments includes interpolating onto a common two-dimensional sample grid (e.g., a planar region). This results in partial images being formed or generated, which are added together.

Accordingly, the A-lines formed from each transmit do not have to follow exactly the same trajectory as A-lines formed in response to other transmits. Accordingly, the A-lines can maintain a good spatial sampling with depth, rather than diverging in a sector scan, as straight, co-linear A-lines. Thus, in various embodiments, the trajectory of the Rx line is changed, thereby effectively changing the overlap of the MLAs from different Tx events over depth.

It should be noted that the various embodiments may be implemented in hardware, software or a combination thereof. The various embodiments and/or components, for example, the modules, or components and controllers therein, also may be implemented as part of one or more computers or processors. The various embodiments and/or components may be implemented in a different order or arrangement. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a floppy disk drive, optical disk drive, and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), ASICs, logic circuits, and any other circuit or processor capable of executing the functions described herein. The above examples are exemplary only, and are thus not intended to limit in any way the definition and/or meaning of the term "computer".

As used herein, the terms "computer," "computing system," "system," "system controller," or "module" may include a hardware and/or software device or system that operates to perform one or more functions. For example, a module or system may include a computer processor, controller, or other logic-based device that performs operations based on instructions stored on a tangible and non-transitory computer readable storage medium, such as a computer memory. Some examples include microcontrollers, reduced instruction set computers (RISC), application specific integrated circuits (ASICs), and logic circuits. In some cases, a module or system may include a hard-wired device that performs operations based on hard-wired logic of the device. The modules shown in the attached figures may represent the hardware that operates based on software or hardwired instructions, the software that directs hardware to perform the operations, or a combination thereof.

In some embodiments, the computing system and/or the modules of the computing system include circuitry that is configured to achieve the actions or functions described herein. For example, the circuitry may be configured to receive inputs (e.g., from a user of the system or from another portion of the computing system), process the inputs, and provide designated outputs. The designated outputs may include signals that have instructions for performing designated actions. The actions may be physical actions or otherwise detectable actions.

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments. The set of instructions may be in the form of a software program. The software may be in various forms such as system software or application software and which may be embodied as a tangible and non-transitory computer readable medium. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the inventive subject matter without departing from its scope. While the dimensions and types of materials described herein are intended to define the parameters of various embodiments, they are by no means limiting and are only example embodiments. Many other embodiments will be apparent to those of skill in the art upon reviewing the above description. The scope of the present application should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

What is claimed is:

1. A method for ultrasound imaging, the method comprising:
obtaining ultrasound data using receive line spacing of receive lines that changes as a function of depth, wherein changing the receive line spacing as the function of depth comprises decreasing the receive line spacing with an increase in depth by applying a dynamic beam steering process on samples of the ultrasound data, and wherein the dynamic beam steering process comprises dynamically changing a beam steering angle;
determining a number of transmit events to combine at each of a plurality of points for use in combining the obtained ultrasound data;
aligning the ultrasound data with time delays computed from a probe geometry used to obtain the ultrasound data; and
combining the aligned ultrasound data to generate an ultrasound image.

2. The method of claim 1, wherein determining the number of transmit events comprises determining the number of transmit events to combine at each of a plurality of points using a signal to noise ratio of the obtained ultrasound data for use in combining partial images to be generated from the obtained ultrasound data.

3. The method of claim 1, further comprising interpolating the obtained ultrasound data on a common two-dimensional grid to form partial images, and wherein the aligned ultrasound data comprises aligned partial images that are combined to generate the ultrasound image.

4. The method of claim 3, wherein the interpolating comprises interpolating a plurality of dynamically beam steered receive lines to the common two-dimensional grid prior to aligning and combining.

5. The method of claim 3, wherein the interpolating comprises coherently interpolating a complex baseband representation of the ultrasound data to transfer the ultrasound data onto the common two-dimensional grid.

6. The method of claim 1, further comprising determining for each of the plurality of points a position in space, determining output pixels for the ultrasound image by selecting a plurality of nearest points from each of a plurality of receive lines, and summing the plurality of nearest points.

7. The method of claim 1, further comprising changing a trajectory of the receive lines to change an overlap thereof from different transmit events over depth.

8. The method of claim 1, wherein the line spacing changes discontinuously as a function of depth.

9. The method of claim 1, wherein the line spacing changes continuously as a function of depth.

10. The method of claim 1, wherein the combining comprises combining a plurality of multi-line acquisitions.

11. The method of claim 1, further comprising determining a number of transmit events to combine at each of the plurality of points using a peak power of an incident waveform at the point of each of the transmit events.

12. The method of claim 1, wherein aligning the ultrasound data comprises computing alignment delays without the generation of a transmit waveform model.

13. An ultrasound system comprising:
a probe configured to acquire ultrasound data;
a controller configured to control acquisition of the ultrasound data by the probe and process the acquired ultrasound data, the controller comprising a retrospective transmit beam forming (RTB) module configured to:
obtain the ultrasound data using receive line spacing of receive lines that changes as a function of depth, wherein the RTB module is configured to decrease the receive line spacing with an increase in depth by applying a dynamic beam steering process on samples of the ultrasound data, and wherein the dynamic beam steering process comprises dynamically changing a beam steering angle; and
determine a number of transmit events to combine at each of a plurality of points for use in combining the obtained ultrasound data, align the ultrasound data with a probe geometry used to obtain the ultrasound data, and combine the aligned ultrasound data to generate an ultrasound image.

14. The ultrasound system of claim 13, wherein the RTB module is further configured to determine the number of transmit events to combine at each of a plurality of points using a signal to noise ratio of the obtained ultrasound data for use in combining partial images to be generated from the obtained ultrasound data.

15. The ultrasound system of claim 13, wherein the RTB module is further configured to interpolate the obtained ultrasound data on a common two-dimensional grid to form partial images and wherein the aligned ultrasound data comprises aligned partial images that are combined to generate the ultrasound image.

16. The ultrasound system of claim 15, wherein the RTB module is further configured to interpolate a plurality of dynamically beam steered receive lines to the common two-dimensional grid prior to aligning and combining.

17. The ultrasound system of claim 15, wherein the RTB module is further configured to coherently interpolate a complex baseband representation of the ultrasound data to transfer the ultrasound data onto the common two-dimensional grid.

18. The ultrasound system of claim 15, wherein the RTB module is further configured to determine for each of the plurality of points a position in space, determine output pixels for the ultrasound image by selecting a plurality of nearest points from each of a plurality of receive lines, and sum the plurality of nearest points.

19. The ultrasound system of claim 13, wherein the RTB module is further configured to change a trajectory of the receive lines to change an overlap thereof from different transmit events over depth.

20. The ultrasound system of claim 13, wherein the RTB module is further configured to change the line spacing discontinuously as a function of depth.

21. The ultrasound system of claim 13, wherein the RTB module is further configured to change the line spacing continuously as a function of depth.

22. The ultrasound system of claim 13, wherein the RTB module is further configured to combine a plurality of multi-line acquisitions.

23. The ultrasound system of claim 13, wherein the RTB module is further configured to determine a number of transmit events to combine at each of the plurality of points using a peak power of an incident waveform at the point of each of the transmit events.

24. The ultrasound system of claim 13, wherein the RTB module is further configured to compute alignment delays without the generation of a transmit waveform model.

25. A non-transitory computer readable storage medium for ultrasound imaging using a processor, the non-transitory computer readable storage medium including instructions to command the processor to:

obtain ultrasound data using receive line spacing of receive lines that changes as a function of depth, wherein changing the receive line spacing as the function of depth comprises decreasing the receive line spacing with an increase in depth by applying a dynamic beam steering process on samples of the ultrasound data, and wherein the dynamic beam steering process comprises dynamically changing a beam steering angle;

determine a number of transmit events to combine at each of a plurality of points for use in combining the obtained ultrasound data;

align the ultrasound data using time delays computed from a probe geometry used to obtain the ultrasound data; and combine the aligned ultrasound data to generate an ultrasound image.

26. The non-transitory computer readable storage medium of claim 25, wherein the instructions command the processor to determine the number of transmit events to combine at each of a plurality of points using a signal to noise ratio of the obtained ultrasound data for use in combining partial images to be generated from the obtained ultrasound data.

27. The non-transitory computer readable storage medium of claim 25, wherein the instructions command the processor to obtain ultrasound data on a common two-dimensional grid to form partial images and wherein the aligned ultrasound data comprises aligned partial images that are combined to generate the ultrasound image.

28. The non-transitory computer readable storage medium of claim 27, wherein the instructions command the processor to interpolate a plurality of dynamically beam steered receive lines to the common two-dimensional grid prior to aligning and combining.

29. The non-transitory computer readable storage medium of claim 27, wherein the instructions command the processor to coherently interpolate a complex baseband representation of the ultrasound data to transfer the ultrasound data onto the common two-dimensional grid.

30. The non-transitory computer readable storage medium of claim 25, wherein the instructions command the processor to determine for each of the plurality of points a position in space, determine output pixels for the ultrasound image by selecting a plurality of nearest points from each of a plurality of receive lines, and sum the plurality of nearest points.

\* \* \* \* \*